United States Patent [19]

Stapp

[11] E Patent Number: Re. 32,289

[45] Reissued Date of Patent: Nov. 18, 1986

[54] CYANOHYDROCARBYLATED ALKOXYLATES AND GLYCERIDES

[75] Inventor: Paul R. Stapp, Bartlesville, Okla.

[73] Assignee: Phillips Petroleum Company, Bartlesville, Okla.

[21] Appl. No.: 745,773

[22] Filed: Jun. 17, 1985

Related U.S. Patent Documents

Reissue of:

[64] Patent No.: 4,455,255
Issued: Jun. 19, 1984
Appl. No.: 371,865
Filed: Apr. 26, 1982

[51] Int. Cl.[4] ..... E21B 43/22; E21B 43/24

[52] U.S. Cl. ..... 166/273; 166/274; 166/275; 252/354; 252/355; 252/8.554; 558/389; 558/402

[58] Field of Search ..... 252/8.55 D, 8.5 C; 166/273, 274, 275; 260/465 D; 252/354, 355

[56] References Cited

U.S. PATENT DOCUMENTS

| | | | |
|---|---|---|---|
| 2,830,018 | 4/1958 | Thompson et al. | 252/8.5 |
| 3,508,612 | 4/1970 | Reisberg et al. | 166/274 |
| 3,799,264 | 3/1974 | Cardenas et al. | 166/275 |
| 3,811,504 | 5/1974 | Flournoy et al. | 166/273 |
| 3,811,505 | 5/1974 | Flournoy et al. | 166/274 |
| 3,811,507 | 5/1974 | Flournoy et al. | 166/274 |
| 3,827,497 | 8/1974 | Dycus et al. | 166/274 |
| 3,858,656 | 1/1975 | Flournoy et al. | 166/274 |
| 3,920,073 | 11/1975 | Holm | 166/274 |
| 3,939,911 | 2/1976 | Maddox, Jr. et al. | 166/274 |
| 3,946,812 | 3/1976 | Gale et al. | 166/274 |
| 3,977,471 | 8/1976 | Gale et al. | 166/273 |
| 4,008,768 | 2/1977 | Birk | 166/274 |
| 4,018,278 | 4/1977 | Shupe | 166/252 |
| 4,059,154 | 11/1977 | Braden, Jr. et al. | 166/274 |
| 4,076,743 | 2/1978 | Koch et al. | 260/501.13 |
| 4,077,471 | 3/1978 | Shupe et al. | 166/252 |
| 4,088,189 | 5/1978 | Shupe | 166/272 |
| 4,110,360 | 8/1978 | Sheldon et al. | 260/465 D |
| 4,120,358 | 10/1978 | Kalfoglou | 166/275 |
| 4,133,826 | 1/1979 | Warnant et al. | 260/465 D |
| 4,138,345 | 2/1979 | Williams | 252/8.55 D |
| 4,154,301 | 5/1979 | Carlin et al. | 166/273 |
| 4,157,115 | 6/1979 | Kalfoglou | 166/274 |
| 4,165,785 | 8/1979 | Schievelbein | 166/274 |
| 4,193,452 | 3/1980 | Wilson et al. | 166/274 |
| 4,203,491 | 5/1980 | Reisberg | 166/274 |

OTHER PUBLICATIONS

Maerker et al., J. Am. Oil Chem, Soc., vol. 45, (1968), 72–75.

*Primary Examiner*—Herbert B. Guynn
*Attorney, Agent, or Firm*—French and Doescher

[57] ABSTRACT

Cyanohydrocarbylated alkoxylates and cyanohydrocarbylated glycerides, their preparation and their use in post primary oil recovery as cosurfactants is described.

21 Claims, No Drawings

CYANOHYDROCARBYLATED ALKOXYLATES AND GLYCERIDES

Matter enclosed in heavy brackets [ ] appears in the original patent but forms no part of this reissue specification; matter printed in italics indicates the additions made by reissue.

The present invention relates to novel cyanohydrocarbylated compounds. In another aspect this invention relates to surfactant systems containing these novel compounds. A further aspect of this invention is the production of the novel compounds. Yet another aspect of this invention relates to tertiary oil recovery processes.

BACKGROUND OF THE INVENTION

Post primary oil recovery by water flooding and surfactant flooding operations are well known processes employed to recover the vast quantities of oil remaining in the formation after primary oil recovery operations. Many different surfactant systems have been described in the prior art for use in surfactant flooding systems. Designing new surfactant systems of high oil recovery efficiency and good phase stability remains a goal in this technology.

THE INVENTION

It is an object of this invention to provide new chemical compositions useful in post primary oil recovery. Another object of this invention is to provide such new compositions which have both a cosurfactant function and a protective agent function in post primary oil recovery operations.

Another object of this invention is to provide a process for the production of such new chemical compositions which is relatively inexpensive and employs readily available starting materials.

Still a further object of this invention is the provision of surfactant systems useful in surfactant flooding operations. Particularly surfactant systems useful in environments comprising hard brines constitute an object of this invention.

Yet another object of this invention is to provide an oil recovery process using the surfactant system of this invention.

These and other objects, advantages, details, features and embodiments of this invention will become apparent to those skilled in the art from the following detailed description of the invention and the appended claims.

In accordance with this invention, two groups of novel chemical compositions are provided which are useful as cosurfactants in post primary oil recovery. These new chemical compositions are cyanohydrocarbylated alkoxylates and cyanohydrocarbylated glycerides as defined more specifically in the following.

CYANOHYDROCARBYLATED ALKOXYLATES

In accordance with a first embodiment of this invention, a group of novel chemical compositions is provided which can be characterized by the following formula

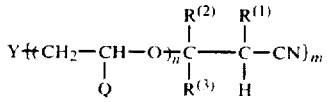

wherein Y and m have one of the following meanings:

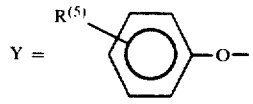

(m = 1)

Y = $R^{(5)}$—O— (m = 1)

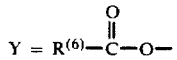

(m = 1)

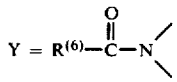

(m = 2)

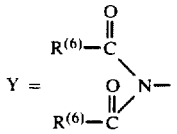

(m = 1)

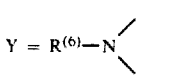

(m = 2)

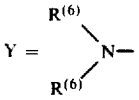

(m = 1)

and wherein Q is hydrogen or methyl, $R^{(1)}$, $R^{(2)}$, $R^{(3)}$, are hydrogen, aryl or alkaryl radicals with 6 to 10 carbon atoms, or alkyl radicals with 1 to 5 carbon atoms, and can be the same or different, $R^{(5)}$ and $R^{(6)}$ are alkyl radicals having 3 to 21 carbon atoms or aryl or alkaryl radicals having 6 to 20 carbon atoms, m is an integer of 1 or 2 as indicated, n is an integer of 1 to 40. The length of the hydrocarbyl portion ($R^{(5)}$ and $R^{(6)}$) of the molecule and n are broadly correlated: longer hydrocarbyl chains require a larger value of n. The preferred cyanohydrocarbylated alkoxylates are those wherein Y is alkylphenoxy or alkoxy. Preferably the radicals $R^{(1)}$, $R^{(2)}$, $R^{(3)}$ are hydrogen. Among the compounds defined, the ethoxylates, i.e., the compounds wherein Q is hydrogen, are preferred. For those compounds, wherein Y is either

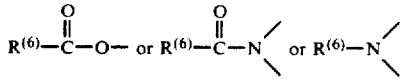

is presently preferred that $R^{(6)}$ is an alkyl radical of 3 to 21 carbon atoms.

CYANOHYDROCARBYLATED GLYCERIDES

In accordance with a second embodiment of this invention, novel cyanohydrocarbylated glycerides are provided. These compounds are broadly characterized by the following formula:

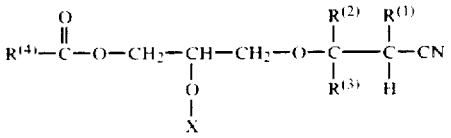

wherein X is hydrogen,

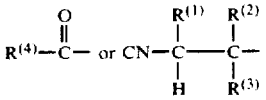

$R^{(4)}$ is an alkyl radical having 3 to 21 carbon atoms, $R^{(1)}$, $R^{(2)}$ and $R^{(3)}$ represent hydrogen, aryl or alkaryl radicals having 6 to 10 carbon atoms or alkyl radical having 1 to 5 carbon atoms, wherein these radicals can be the same or different. Among the glycerides defined above, the monoglycerides, i.e., the compounds wherein X is the cyanohydrocarbyl group as defined, are presently preferred.

Mixture of two or more of the novel cyanohydrocarbylated compounds are also within the scope of this invention.

CYANOHYDROCARBYLATION PROCESS

In accordance with a further embodiment of this invention, a process to produce the novel compositions as defined above is provided. This process can be broadly described as the reaction between alkoxylated compounds and an $\alpha,\beta$-unsaturated nitrile in the presence of a base catalyst. More specifically, the process of this invention for the production of cyanohydrocarbylated ethoxylates comprises the step of reacting a compound having the formula

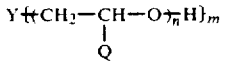

wherein n, m, Q and Y have the meaning defined above with an unsaturated nitrile characterized by the formula

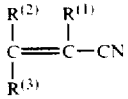

wherein $R^{(1)}$, $R^{(2)}$, and $R^{(3)}$ are as defined above.

Similarly, the process of this invention to produce the glycerides involves the step of reacting a mono or diglyceride characterized, respectively, by the formula

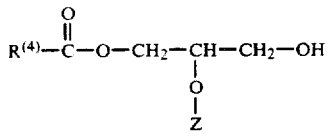

wherein Z is hydrogen or

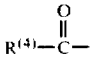

with an unsaturated nitrile as defined above.

The cyanohydrocarbylation is carried out in accordance with this invention in the presence of a base. This base can be any of the strong bases known to catalyze the substitution reaction here involved. The base is preferably selected from the group consisting of the alkali metal hydroxides and tertiary amines. Most preferably, the reaction is carried out in the presence of sodium hydroxide and/or potassium hydroxide. Other bases well known in the art can also be used such as tertiary amines including triethylamine, pyridine, quinoline and the like.

Suitable solvents include hydrocarbons, preferably aromatic hydrocarbons, ethers, esters and halogenated hydrocarbons such as benzene, toluene, xylene, pentane, heptane, tetrahydrofuran, dioxane, methylene chloride, carbon tetrachloride, ethyl acetate, butyl acetate, and 1,2-dimethoxyethane. The ingredients involved in the process of this invention are employed in ranges that are not overly critical but generally within the following limits

| | mole hydroxyl containing compound / mole nitrile | |
|---|---|---|
| | Broad | Preferred |
| Mole ratio alkoxylate or respectively glyceride:unsaturated hydrocaryl nitrile | 10:1 to 1:10 | 2:1 to 1:2 |

The base is present in a 0.1 to 20 mol. % level based on the limiting reagent.

The cyanohydrocarbylation reaction is carried out under conditions which are also not critical. The conditions of temperature and pressure generally are such that the reagents involved remain in the liquid phase. As a general rule the temperature will be in the range of 0° to 100° C. and the pressure will be sufficient to maintain the reactant mass in essentially a liquid state. The reaction duration will depend primarily upon economic considerations. Typical reaction times are in the range of several minutes to 24 hours.

While it is possible to employ the reaction product without any further separation in certain applications, it is possible to remove the base catalyst from the reaction mixture. This removal of the base catalyst can be achieved by acidification to a pH of about 7 with an organic acid such as acetic acid. If desired, the cyanohydrocarbylated compound can also be separated from the unreacted nitrile and the unreacted alkoxylate or respectively glyceride. This separation can be done by standard techniques including distillation to remove volatiles such as solvent and unreacted nitrile followed by liquid-liquid extraction.

SURFACTANT SYSTEM

In accordance with a third embodiment of this invention, a surfactant system effective for enhanced oil recovery is provided. This system is an aqueous saline surfactant mixture comprising the novel composition of this invention and a metal hydrocarbyl sulfonate.

The metal hydrocarbyl sulfonate used in the surfactant of this invention can be broadly characterized by the formula $(R—CH_2—A—SO_3)_nM$ wherein n is the valence of M, i.e., 1 or 2, A represents an aromatic, alkenylene or alkylene radical having 6 to 30 carbon atoms or a valence bond. The latter groupings arising, e.g., by interactions of a sulfonating agent such as $SO_3$ with olefinic linkages present in the sulfonatable oil feedstock. When A represents an aromatic radical, it is contemplated that in addition to the hydrocarbyl grouping $RCH_2$— there may or may not be other similar moieties. The radical A can be derived from benzene or alkylbenzenes as well as from polynuclear aromatics such as naphthalene, anthracene, and phenanthrene and alkylated derivatives thereof. The $RCH_2$— grouping represents an alkyl radical of 4 to 30 carbon atoms and the radical R is a hydrocarbyl radical of 3 to 30 carbon atoms, preferably can be a straight chain or branched alkyl radical. M represents ammonium ion, and alkali metal or alkaline earth metal cations. Preferably M represents sodium because of price and availability. Among the metal hydrocarbyl sulfonates suitable as surfactant in the system of this invention, the arene sulfonates, and particularly the petroleum sulfonates are presently preferred. Petroleum sulfonates are well known in the art and are obtained by a sulfonation of aromatic petroleum fractions followed by neutralization with ammonium hydroxide or the hydroxides of alkali metals or alkaline earth metals. These petroleum sulfonates are commercially available products. The presently preferred petroleum sulfonates used in the surfactant system of this invention have an average equivalent weight in the range of 325 to 500. Best enhanced oil recovery results with presently known reservoirs are believed to be obtainable from surfactant systems employing such sodium petroleum sulfonates.

Most preferably the surfactant system of this invention is an aqueous system. Although optionally a protective agent can be added to this system, the novel compositions of this invention incorporated in the surfactant system also have protective agent.

TABLE I

| | | |
|---|---|---|
| Water | 100 | 100 |
| Metal hydrocarbyl sulfonate (active parts by weight) | 0.1-15 | 1-12 (particularly 2-5) |
| Cyanohydrocarbylated alkoxylate/glyceride | 0.1-20 | 0.2-7 |
| Protective Agent (optional) | 0.01-3 | 0.05-2 |
| NaCl | 0.1-10 | 0.1-8 |

Since this surfactant system is particularly applicable in environments of hard brines and the aqueous fluid used in the on site production of the surfactant system is therefore generally also a hard brine it is particularly contemplated and within the scope of this invention that the surfactant system based on 100 parts by weight of water will also contain ions in the following quantities which render the water or the brine "hard":

TABLE II

| Ingredient (parts by weight) | Broad Range | Preferred Range |
|---|---|---|
| "Hard" Ions ($Mg^{++}$, $Ca^{++}$, $Ba^{++}$, etc.) | 0-10,000 ppm | 2-1000 ppm |

The novel compositions of this invention employed in the surfactant system of the invention have the function of a cosurfactant. It is thus in accordance with this invention not necessary to employ a cosurfactant in addition to the compounds of this invention. However, under certain conditions and in particular environments during post primary oil recovery, it may be desirable to employ the novel compositions of this invention, i.e. the cyanohydrocarbylated alkoxylates or glycerides, respectively, not only together with conventional hydrocarbyl sulfonates as defined but also together with a further cosurfactant. Such a cosurfactant is preferably one that is selected from the group consisting of organonitriles and alcohols. The nitriles can be broadly characterized as organonitriles having 1 to 3 —CN groups attached to carbon atoms in compounds containing up to 13 carbon atoms and up to 4 oxygen and/or sulfur atoms and up to 4 additional nitrogen atoms. The preferred nitriles are acetonitrile, propionitrile, butyronitrile, α-methyleneglutaronitrile, tridecanenitrile, benzonitrile, phenylacetonitrile, acrylonitrile, methacrylonitrile, vinylacetonitrile, succinonitrile, 1,3dicyanopropene, 1,3-dicyano-3-butene, tris(cyanoethyl)methane, 1,1-decyanoethane and mixtures thereof. The preferred nitrile when used in addition to the novel compositions of this invention is acrylonitrile. The alcohols contemplated as cosurfactants in accordance with this invention include alcohols having 3 to 12 carbon atoms. Examples of useful alcohols which can be employed as cosurfactants include isopropanol, 1-butanol, isopentyl alcohol, isobutyl alcohol, hexanol, octanol, dodecanol, heptanol, decanol and mixtures thereof. The preferred alcohol cosurfactant is isobutyl alcohol.

When employed, the cosurfactant is used in a quantity relative to the sulfonate surfactant within the following ranges:

TABLE III

| | Broad Range | Preferred Range |
|---|---|---|
| Hydrocarbon sulfonate* | 1-12 | 2-5 |
| Cosurfactant | 0-15 | 0-15 |

*Quantities are shown in wt. %.

OIL RECOVERY PROCESS

A further embodiment of this invention resides in an oil recovery process. This process involves generally the conventional steps of post primary oil recovery and distinguishes over the known procedures primarily in the use of the novel compounds defined above and in the surfactant system employing these novel compounds.

PREFLUSH

It is optional, although not necessary, to carry out a preflush step preceding the further oil recovery operation. Such preflush operations are known in the art. Generally, a brine compatible with the surfactant system is injected via at least one injection well into the subterranean formation. Such a brine typically contains 2000-50,000 ppm salts, predominantly sodium chloride. Preferably a brine solution as utilized in the production of the surfactant system is also used in this preflush step.

The quantity of the preflush employed will generally be in a range of about 0.01 to 2, preferably 0.25 to 1 pore volume, based on the total pore volume of the formation or reservoir subjected to the recovery.

SURFACTANT FLOODING

After the optional preflush step the surfactant fluid of this invention is injected into the reservoir via at least one injection well. The surfactant system is injected in an amount usually in the range of about 0.001 to 1.0, preferably 0.01 to 0.25 pore volume based again on the pore volume of the total treated and produced formation.

The preferred operation makes use of the surfactant system in a manner that a multiphase system including at least one microemulsion phase is formed in the formation. Usually the surfactant system contains as the main ingredients water, the surfactant including the cyanohydrocarbylated alkoxylate or respectively glyceride and optionally the cosurfactant. These ingredients are thoroughly mixed and then introduced into the formation via one or more injection wells. However, the in-situ formation of a microemulsion in the formation, e.g. by simultaneous but unmixed injection or by alternating the injection of surfactant and cosurfactant is also within the scope of this invention.

The term "cosurfactant" as herein used is intended to encompass both the novel compositions of this invention and any additional cosurfactant employed.

Generally, the microemulsion is formed in the reservoir after the surfactant system is injected as a solution containing surfactant and cosurfactant in brine.

The present invention can be utilized for a variety of subterranean reservoirs. The invention is, however, particularly preferred in reservoirs containing hard brine connate water. Such hard brines are characterized by a high content of $Mg++$ and $Ca++$ ions in the reservoir water. Typical hard brines contain more than 100 ppm of $Ca++$ and/or $Mg++$.

If additional protective agents are employed in the surfactant system of this invention, they are utilized in the quantities shown above in addition to the novel compositions of this invention which, as mentioned above, also have protective agent function. Examples for such protecting agents are polyethoxylated fatty alcohols and polyethoxylated alkylphenols. In addition, the sodium salts of sulfated polyethoxylated fatty alcohols and polyethoxylated alkylphenols are known in the art to function as protective agents. These additionally employed protective agents can be the unreacted starting materials of the cyanohydrocarbylation reaction.

MOBILITY BUFFER

Following the surfactant slug it is presently preferred, although not necessary, to inject a mobility buffer solution into the reservoir. This buffer helps prevent fingering and enhances the efficiency of the oil recovery. Buffer solutions are aqueous solutions of polymeric viscosifiers of other thickening agents. Examples of useful mobility buffers are aqueous fluids containing mobility reducing agents such as high molecular weight partially hydrolyzed polyacrylamides, biopolysaccharides, soluble cellulose ethers and the like. The mobility buffer comprises 50 to 20,000, preferably 200 to 5,000 ppm of the mobility reducing agent in the fluid.

The concentration of the thickening agent in the mobility buffer fluid can remain constant over the injection period or the mobility buffer slug can be "graded", i.e., the viscosifier concentration starts out at a relatively high level at the beginning of the injection and the concentration tapers off toward the end of the injection. As an example, the aqueous mobility buffer slug can start with a concentration of 2,500 ppm of polyacrylamide and be graded back by continuous dilution to 250 ppm of polyacrylamide. The "grading" of mobility buffer fluids is well-known in the art.

The invention will be still more fully understood from the following detailed examples which are intended for illustrative purposes only and not for an undue limitation of the scope of this invention.

EXAMPLE I

This example describes the cyanoethylation of ethoxylated 2-ethyl-1-hexanol (E.O.=10, i.e., the average number n, see formula above, of ethylene oxide units/mol of alcohol was 10). A charge of 114 g (0.2 mol, formula wt of 570) of ethoxylated 2-ethyl-1-hexanol, 1 g of potassium hydroxide pellets (85 wt % KOH) and 200 mL of toluene was placed in a glass reactor vessel and the mixture was stirred until all the KOH pellets dissolved. About 100 mL of this mixture was evaporated on a rotary evaporator to remove water and a portion of the toluene. The dried liquid residue was transferred to an Erlenmeyer flask. A 16.4 mL (13.25 g, 0.25 mol) portion of acrylonitrile was added dropwise over a period of about 10 minutes to the stirred toluene solution of the ethoxylated 2-ethyl-1-hexanol and the mixture became dark red. After the addition of acrylonitrile, this mixture was stirred at room temperature for about 24 hours. After the addition of 2 milliliters of acetic acid, the mixture was concentrated on a rotary evaporator to give 128.2 g of a dark-colored oily residue. An elemental analysis on this residue gave the following results: Found: % C, 59.97; % H 9.88; % N, 2.72. Calc'd for $C_{31}H_{61}O_{11}N$ (formula wt 623): % C, 59.71; % H, 9.79; % N, 2.25. The formula $C_{31}H_{61}O_{11}N$ corresponds to an "average" structure resulting from the chemical combination of one mole of acrylonitrile per mole of the ethoxylated (E.O.=10) 2-ethyl-1-hexanol.

EXAMPLE II

This example describes the cyanoethylation of ethoxylated 2-ethyl-1-hexanol (E.O.=5, i.e., the average number of ethylene oxide units/mol of alcohol was 5). A charge of 175 g (0.5 mol, formula wt of 350) of ethoxylated 2-ethyl-1-hexanol, 3 g of potassium hydroxide pellets (85 wt % KOH) and 100 mL of toluene was placed in a 500 mL round-bottomed flask equipped with water-cooled reflux condenser, Dean-Stark water separation trap and magnetic stirrer. This stirred mixture was boiled for two hours under a $N_2$ atmosphere to azeotropically remove water. The cooled reaction mixture was transferred to an Erlenmeyer flask equipped with a thermometer and a dropping funnel containing 35 mL (27.9 g, 0.53 mol) of acrylonitrile. The acrylonitrile was added dropwise to the stirred reaction mixture over a period of about 30 minutes during which time the temperature was maintained below about 45° C. After the addition of 5 mL of acetic acid, the mixture was transferred to a rotary evaporator and concentrated to a dark-colored residue which weighed about 207.5 g. An elemental analysis on this residue gave the following results: Found % C 61.3; % H, 10.0; % N, 3.48. Calc'd for $C_{21}H_{41}O_6N$ (formula wt 403): % C, 62.53; % H, 10.17; % N, 3.47. The formula $C_{21}H_{41}O_6N$ corresponds to an "average" structure resulting from the chemical combination of one mol of acrylonitrile per mol of the ethoxylated (E.O.=5) 2-ethyl-1-hexanol.

EXAMPLE III

This example describes the cyanoethylation of ethoxylated 2-ethyl-1-hexanol (E.O.=2, i.e., the average number of ethylene oxide units/mol of alcohol was 2).

A charge of 43.6 g (0.2 mol, formula wt of 218) of ethoxylated 2-ethyl-1-hexanol, 1 g of potassium hydroxide pellets (85 wt % KOH) and 200 mL of toluene was placed in a glass reactor vessel and the mixture was stirred until all the KOH pellets dissolved. This mixture was concentrated on a rotary evaporator to remove water and part of the toluene. The dried liquid residue was transferred to an Erlenmeyer flask. A 16.4 mL (13.25 g, 0.25 mol) portion of acrylonitrile was added dropwise over a period of about 20 minutes to the stirred toluene solution of the ethoxylated 2-ethyl-1-hexanol. After the addition of acrylonitrile, the mixture was stirred at room temperature for about 14 hours. Two milliliters of acetic acid were added to the mixture before concentrating the mixture on a rotary evaporator to give 58.5 g of a dark-colored oily residue. An elemental analysis on this residue gave the following results: Found: % C, 64.08; % H, 10.42; % H, 5.35. Calc'd for $C_{15}H_{29}O_3N$ (formula wt 271): % C, 66.4; % H, 10.7; % N, 5.17. The formula $C_{15}H_{29}O_3N$ corresponds to an "average" structure resulting from the chemical combination of one mole of acrylonitrile per mol of ethoxylated (E.O.=2) 2-ethyl-1-hexanol. Equilibration of this cyanoethylated cosurfactant with petroleum sulfonate and simulated live North Burbank Unit crude oil over a range of salinities established the optimal salinity of this system to be 1.3 wt % NaCl.

CORE CONDITIONING

The following conditioning procedure was used in preparing the waterwet Berea sandstone cores for surfactant flooding tests.

Berea sandstone cores measuring approximately 3 feet in length and 3 inches in diameter were dried under vacuum for 24 hours at 250° F. Polycarbonate disc end plates with centrally located ⅛" threaded openings were secured to each end of the core with epoxy adhesive before applying an epoxy coating to the outside surface of the core. The epoxy coating material was formulated by mixing 550 g of a commercially available epoxy resin, 50 g of a suitable activator and 140 g diatomaceous earth. This mixture was stirred until smooth before applying to the surface of the core. The cores were rotated continuously as the epoxy mixture was applied with a 2" paint brush. Four gauze strips measuring 2"×12" were applied to the core in the following manner: a first gauze strip was applied to the core and covered with epoxy as the core was rotated; the remaining three strips were then individually incorporated in a similar manner. The core coating was cured over a period of about 4 hours at ambient temperature as the core was rotated. One-eighth inch male connector fittings were placed on each end of the core and pipe plug caps were put on the core.

The core was weighed to determine the dry weight before being saturated with brine of the desired concentration. A vacuum of about 1 mm was pulled on the core before saturating the core with approximately 1,000 mL of brine. After saturation, approximately 100 to 200 mL of brine were pumped through the core before determining the original permeability to water. A 1 mL portion of effluent brine was collected from the saturated core and thereafter during a period of one minute, the volume of additional effluent collected and the pressure in psi were recorded. With these values the original permeability to water, e.g., on the order of 3.2 ml/min at 43 psi could be recorded. The pore volume of the core was calculated by the relationship:

$$\frac{\text{Brine Saturated Core Wt (g)} - \text{Dry Core Wt (g)}}{\text{Brine Density (g/mL)}} = \text{Core Pore Volume (mL)}$$

The brine-saturated core was oil flooded in the conventional manner until oil break-through became detectable by the presence of alternate globules of oil and water in the effluent line. The oil flood was carried out to completion by the 24 hour recycling of oil through the core to remove all the displaceable water. The total water displaced, i.e., water displaced at the point of oil break-through and water displaced by the 24 hour recycle procedure was recorded as water displaced by oil flood. If desired, oil permeability was determined in a manner analogous to that used above for establishing original permeability to water. Prior to waterflood, the effluent line was air blown to remove oil.

The oil-flooded core was waterflooded in the conventional manner until water break-through became detectable by the presence of alternate globules of oil and water in the effluent line. The waterflood was carried to completion by the 24 hour recycling of water through the core to remove all of the displaceable oil. The total oil displaced, i.e., oil displaced at the point of water break-through and oil displaced by the 24 hour recycle procedure was recorded as oil displaced by waterflood. If desired, water permeability after waterflood can be determined in a manner analogous to that used above for original permeability to water. The residual oil volume remaining in the core was calculated by subtracting the oil volume displaced by the waterflood from the water volume displaced by the oilflood. At this point, the core simulateld an oil reservoir which has been exhaustively waterflooded. Cores were routinely conditioned in this manner prior to carrying out surfactant flood tests.

EXAMPLE IV

This example demonstrates the oil recovery effectiveness of a high-salinity-tolerant surfactant system containing a petroleum sulfonate surfactant and a cosurfactant derived from an ethoxylated 2-ethyl-1-hexanol and acrylonitrile. The preparation of said cosurfactant from the reaction of acrylonitrile and ethoxylated 2-ethyl-1-hexanol (containing an average of 10 ethylene oxide units, E.O.=10) is described in Example I. Waterflood residual oil from a waterwet Berea sandstone core was recovered by surfactant flooding in the conventional manner, i.e., sequential injection of the inventive surfactant system and a thickened aqueous mobility buffer slug of polyacrylamide graded back logarithmically with Arkansas-Burbank water.

The surfactant slug had the following composition:

8.71 g Witco 10-410 (62 wt % active petroleum sulfonate)

4.50 g Cyanoethylated Polyethoxylated 2-Ethyl-1-hexanol (Ex. I)

10.50 g NaCl 126.29 g Arkansas-Burbank water

Thus, each component was present in the following weight Percentages:

Petroleum sulfonate (active basis): 3.6 wt %

Cyanoalkylated Cosurfactant: 3.0 wt %

Sodium Chloride (Optimal Salinity): 7.0 wt %

Arkansas-Burbank Water: 86.4 wt %

The pore volume of the 3"×3' cylindrical Berea sandstone core was 806 mL. Since a 60.5 mL slug of the above surfactant composition was injected, the slug size expressed in terms of core pore volume was 7.5% PV. The surfactant slug was followed by 403 mL (0.5 PV) of Betz Hi Vis polyacrylamide (1700 ppm) in Arkansas-Burbank water graded back logarithmically with Arkansas-Burbank water.

In preparing the core, 567.3 mL of water was displaced from the water-saturated core by oilflood indicating the introduction of approximately 567.3 mL of oil into the core. Subsequent waterflood resulted in approximately 269 mL of oil being displaced from the core leaving approximately 298.3 mL of waterflood residual oil in the Berea sandstone core prior to the surfactant flood.

In the course of the surfactant flood, a total effluent of 2.4 pore volumes (ca. 1940 mL) was collected which contained 184.1 mL of tertiary oil representing 61.7% of the waterflood residual oil.

EXAMPLE V

This example demonstrates the oil recovery effectiveness of a surfactant system containing a petroleum sulfonate surfactant and a cosurfactant derived from an ethoxylated 2-ethyl-1-hexanol and acrylonitrile. The preparation of said cosurfactant from the reaction of acrylonitrile and ethoxylated 2-ethyl-1-hexanol (containing an average of 5 ethylene oxide units, E.O.=5) is described in Example II. Waterflood residual oil from a waterwet Berea sandstone core was recovered by surfactant flooding in the conventional manner, i.e., sequential injection of the inventive surfactant system and a thickened aqueous mobility buffer slug of polyacrylamide graded back logarithmically with Arkansas-Burbank water.

The surfactant slug had the following composition:

8.71 g Witco 10-410 (62 wt % active petroleum sulfonate)

4.50 g Cyanoethylated Polyethoxylated 2-ethyl-1-hexanol (Ex. II)

3.75 g NaCl 133.04 g Arkansas-Burbank water

Thus, each component was present in the following weight percentage:

Petroleum sulfonate (active basis): 3.6

Cyanoethylated Cosurfactant: 3.0

Sodium chloride (Optimal Salinity): 2.5

Arkansas-Burbank Water: 90.9

The pore volume of the 3"×3' cylindrical Berea sandstone core was 781 mL. Since a 58.6 mL slug of the above surfactant composition was injected, the slug size expressed in terms of core pore volume was 7.5% PV. The surfactant slug was followed by 390 mL (0.5 PV) of Betz Hi Vis polyacrylamide (1,700 ppm) in Arkansas-Burbank water graded back logarithmically with Arkansas-Burbank water.

In preparing the core, 532 mL of water was displaced from the water-saturated core by oilflood indicating the introduction of approximately 532 mL of oil into the core. Subsequent waterflood resulted in approximately 240.3 mL of oil being displaced from the core leaving approximately 291.7 mL of waterflood residual oil in the Berea sandstone core prior to the surfactant flood.

In the course of the surfactant flood, a total effluent of 2.33 pore volumes (ca. 1820 mL) was collected which contained 251.9 mL of tertiary oil representing 86.3% of the waterflood residual oil.

Reasonable variations and modifications which will become apparent to those skilled in the art can be made in this invention without departing from the spirit and scope thereof.

That which is claimed is:

1. Surfactant composition comprising (a) a metal hydrocarbyl sulfonate (b) a cyanohydrocarbylated alkoxy composition having the formula:

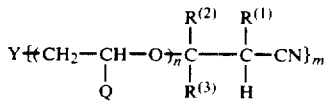

wherein m is 1 or 2, n is an integer of 1 to 40 and wherein Y has one of the following meanings:

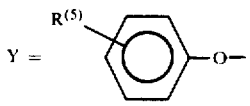

(m = 1)

Y = $R^{(5)}$—O— (m = 1)

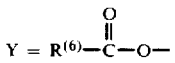

(m = 1)

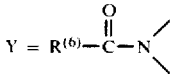

(m = 2)

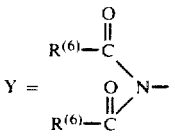

(m = 1)

(m = 2)

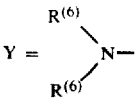

(m = 1)

and wherein

Q is hydrogen or methyl, $R^{(1)}$, $R^{(2)}$, $R^{(3)}$, which can be same or different, are hydrogen, aryl or alkaryl radicals with 6 to 10 carbon atoms, or alkyl radicals of 1 to 5 carbon atoms, $R^{(5)}$ and $R^{(6)}$ are aryl or alkaryl radicals with 6 to [10] *20* carbon atoms or alkyl radicals with [1] *3* to [5] *21* carbon atoms.

2. Surfactant composition in accordance with claim 1 wherein said metal hydrocarbyl sulfonate is a petroleum sulfonate.

3. Surfactant composition in accordance with claim 1 further comprising an aqueous fluid selected from the group consisting of fresh water, brine and hard brine.

4. Surfactant composition in accordance with claim 1 wherein Q is hydrogen.

5. Surfactant composition comprising (a) a metal hydrocarbyl sulfonate (b) a cyanohydrocarbylated glyceride having the formula

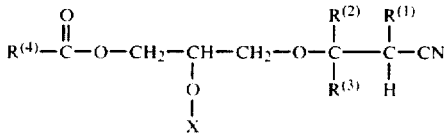

wherein X is hydrogen,

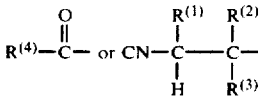

$R^{(1)}$, $R^{(2)}$ and $R^{(3)}$, which can be the same or different, are hydrogen, aryl or alkaryl radicals with 6 to 10 carbon atoms, or alkyl radicals have 1 to 5 carbon atoms, $R^{(4)}$ is an alkyl radical with 3 to 21 carbon atoms.

6. Surfactant composition in accordance with claim 5 wherein said metal hydrocarbyl sulfonate is a petroleum sulfonate.

7. Surfactant composition in accordance with claim 5 further comprising an aqueous fluid selected from the group consisting of fresh water, brine and hard brine.

8. Process for hydrocarbon recovery from subterranean formation comprising (a) injecting a surfactant system comprising a metal hydrocarbyl sulfonate and a cyanohydrocarbylated alkoxylate composition into said formation via at least one injection well, said cyanohydrocarbylated alkoxylate composition having the general formula

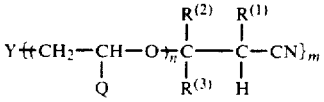

wherein m is 1 or 2, n is an integer of 1 to 40 and wherein Y has one of the following meanings:

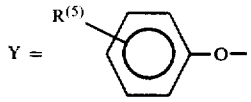

(m = 1)

$Y = R^{(5)}-O-$ (m = 1)

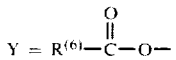

(m = 1)

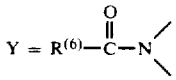

(m = 2)

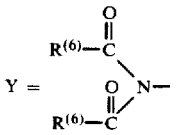

(m = 1)

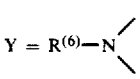

(m = 2)

-continued

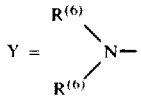

(m = 1)

and wherein Q is hydrogen or methyl, $R^{(1)}$, $R^{(2)}$ $R^{(3)}$, which can be same or different, are hydrogen, aryl or alkaryl radicals with 6 to 10 carbon atoms, or alkyl radicals of 1 to 5 carbon atoms, $R^{(5)}$ and $R^{(6)}$ are aryl or alkaryl radicals with 6 to 20 carbon atoms or alkyl radicals with 3 to 21 carbon atoms, (b) causing the so injected surfactant system to move from the injection well toward one or more production wells displacing hydrocarbon present in said formation, (c) recovering displaced hydrocarbon from at least one of said production wells.

9. Process in accordance with claim 8 wherein a mobility buffer fluid is injected into said formation following said surfactant system.

10. Process in accordance with claim 9 wherein an aqueous drive fluid is injected into said subterranean formation following said mobility buffer fluid.

11. Process in accordance with claim 8 wherein said surfactant system is injected into a formation containing hard brine.

12. Process in accordance with claim 8 wherein a cyanohydrocarbylated alkoxylate composition is employed in which Q is hydrogen.

13. Process in accordance with claim 8 wherein a cyanohydrocarbylated alkoxylate composition is employed wherein $R^{(1)}$, $R^{(2)}$ and $R^{(3)}$ are hydrogen and Y is alkylphenoxy or alkoxy.

14. Process in accordance with claim 8 wherein a cyanohydrocarbylated alkoxylate composition is employed wherein Y is an amine or amide or carboxyl group and $R^{(6)}$ is alkyl.

15. Process in accordance with claim 8 wherein a cyanohydrocarbylated alkoxylate composition is employed wherein n is 1 to 40.

16. A process for hydrocarbon recovery from subterranean formation comprising (a) injecting a surfactant system comprising a metal hydrocarbyl sulfonate and a cyanohydrocarbylated glyceride into said formation via at least one injection well, said cyanohydrocarbylated glyceride having the formula

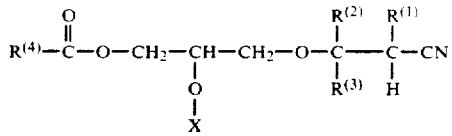

wherein X is hydrogen,

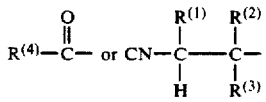

$R^{(1)}$, $R^{(2)}$ and $R^{(3)}$, which can be the same or different, are hydrogen, aryl or alkaryl radicals with 6 to 10 carbon atoms, or alkyl radicals have 1 to 5 carbon atoms, $R^{(4)}$ is an alkyl radical with 3 to 21 carbon atoms, (b) causing the so injected surfactant system to move from the injection well toward one or more production wells displacing hydrocarbon present in said formation.

(c) recovering displaced hydrocarbon from at least one of said production wells.

17. A process in accordance with claim 16 wherein a mobility buffer fluid is injected into said subterranean formation following said surfactant system.

18. A process in accordance with claim 17 wherein an aqueous drive fluid is injected into said subterranean formation following said mobility buffer fluid.

19. A process in accordance with claim 16 wherein said surfactant system is injected into a formation containing hard brine.

20. A process in accordance with claim 16 wherein said cyanohydrocarbylated glyceride is one in which $R^{(1)}$, $R^{(2)}$, $R^{(3)}$ are hydrogen.

21. Surfactant composition in accordance with claim 5 wherein $R^{(1)}$, $R^{(2)}$ and $R^{(3)}$ are each hydrogen.

* * * * *